US00PP33281P2

(12) United States Plant Patent
Olesen

(10) Patent No.: US PP33,281 P2
(45) Date of Patent: Jul. 27, 2021

(54) MINIATURE ROSE PLANT NAMED 'POULPAR125'

(50) Latin Name: *Rosa hybrida*
Varietal Denomination: Poulpar125

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 16/873,990

(22) Filed: Sep. 3, 2020

(51) Int. Cl.
*A01H 5/02* (2018.01)
*A01H 6/74* (2018.01)

(52) U.S. Cl.
USPC ..... Plt./124

(58) Field of Classification Search
USPC ..... Plt./101, 116, 117, 123, 124
See application file for complete search history.

(56) References Cited

PUBLICATIONS

Poulsen Roser. 2020. citation for 'Poulpar125'. https://www.poulsenroser.dk/en/roses/ShowProduct/77685. retrieved Dec. 2, 2020. 1 page. (Year: 2020).*

* cited by examiner

*Primary Examiner* — Susan McCormick Ewoldt
*Assistant Examiner* — Karen M Redden

(57) ABSTRACT

A new garden rose plant of the Miniature class which has abundant, white flowers and attractive foliage. This new and distinct variety has shown to be uniform and stable in the resulting generations from asexual propagation.

1 Drawing Sheet

Botanical designation: *Rosa hybrida.*
Variety denomination: 'Poulpar125'.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2014 and the resulting seeds were planted in a controlled environment in Fredensborg, Denmark. The new variety, named 'Poulpar125', originated as a single seedling from the stated cross.

The new variety may be distinguished from its male pollen parent and female seed parent primarily by the following characteristics. The male pollen parent plant has white flowers and grows to a height of 55 cm while the new variety has white flowers and grows to a height of 21 cm. The female seed parent plant has white flowers with about 30 petals while the new variety has white flowers with 68 petals.

The objective of the hybridization of this rose variety was to create a new and distinct variety with unique qualities, such as:

1. Uniform and abundant white flowers;
2. Vigorous, but compact growth when propagated on its own roots;
3. Exceptional disease resistance.

This combination of qualities is not present in previously available commercial cultivars of this type, known to the inventor, and distinguish 'Poulpar125' from all other varieties of which we are aware.

As part of the rose development program, Mogens N. Olesen germinated the seeds from the aforementioned hybridization during winter of 2014 and conducted evaluations on the resulting seedlings in a controlled environment in Fredensborg, Denmark. 'Poulpar125' was selected in the spring of 2015 by the inventor as a single plant from the progeny of the aforementioned hybridization.

Asexual reproduction of 'Poulpar125' by rooted cuttings was first done by Mogens N. Olesen in the nursery in Fredensborg, Denmark in July, 2015. This initial and other subsequent asexual propagations conducted in controlled environments have demonstrated that the characteristics of 'Poulpar125' are true to type and are transmitted from one generation to the next.

DESCRIPTION OF THE DRAWING

The accompanying color illustration shows as true as is reasonably possible to obtain in color photographs of this type, the typical characteristics of the buds, flowers, leaves, and stems, of 'Poulpar125'. Specifically illustrated in the drawing are flowers at various stages of development, flower bud, sepals and petals detached revealing reproductive flower parts, bare stem, juvenile growth, and mature leaf Plants shown are 12 months old.

DETAILED DESCRIPTION OF THE VARIETY

The following is a description of 'Poulpar125', as observed in its growth outdoor in Odense Denmark. Observed plants are 12 months old and were grown on their own roots in 24 cm containers. Color references are made using The Royal Horticultural Society (London, England) Colour Chart, 2001, except where common terms of color are used.

For a comparison, several physical characteristics of the rose variety 'Poulpar068', U.S. Plant Pat. No. 23,396 are compared to 'Poulpar125' in Chart 1.

CHART 1

| | 'Poulpar125' | 'Poulpar068' |
|---|---|---|
| Petal Count | 68 | 35 |
| Flower Diameter | 50 mm | 65 mm |
| General Tonality of Flower Color | White Group 155B | White Group 155A |

FLOWER AND FLOWER BUD

Blooming habit: Continuous.

Flower bud:

*Size.*—Upon opening, 20 mm in length from base of receptacle to end of bud. Bud diameter is 10 mm.

*Bud form.*—Urceolate.

*Bud color.*—As sepals divide petals are White Group 155B.

*Sepal inner surface.*—Color: Yellow-Green Group 146A. Surface: Lightly pubescent.

*Sepal outer surface.*—Color: Yellow-Green Group 144A. Texture: Smooth.

*Sepal shape.*—Apex: Cirrhose. Base: Flat at union with receptacle.

*Sepal margin.*—Margins have strong foliaceous appendages on three of the five sepals.

*Sepal size.*—25 mm long, 8 mm wide.

*Receptacle.*—Texture: Smooth. Size: 6 mm in height, 9 mm wide. Color: Yellow-Green Group 144A. Shape: Funnel.

*Pedicel.*—Surface: Smooth. Length: About 22 mm. Diameter: 2.5 mm on average. Color: Yellow-Green Group 144B. Strength: Strong.

*Peduncle.*—Length: 1 to 2 cm. Diameter: About 3 mm. Color: Yellow-Green Group 145A. Texture: Smooth.

Flower bud development: Flower buds are borne singly and in clusters of 3 to 5 flower buds per stem.

Flower bloom:

*Fragrance.*—None.

*Duration.*—The blooms have a duration on the plant of approximately 21 days. Petals fall cleanly away from plant after flowers have fully matured.

*Size.*—Flower diameter is 50 mm when open. Flower depth is 20 mm.

*Flower shape.*—High centered, very double, with a high pointed center which is tightly closed.

*Shape of flower, side view.*—The upper portion is convex. The lower portion is flat.

Petalage: Under normal conditions, flowers have about 68 petals.

General tonality of flower: Open flowers are White Group 155B.

Petal color:

*Upon opening, outer petals.*—Upper surface: White Group 155B. At the basal zone Green-White Group 157D. Lower surface: White Group 155B. At the basal zone Green-White Group 157A.

*Upon opening, inner petals.*—Upper surface: White Group 155B. At the basal zone Green-White Group 157D. Lower surface: White Group 155B. At the basal zone Green-White Group 157A.

*Basal petal spots, upon opening.*—No distinctive coloration at the petal base observed.

*After opening, outer petals.*—Upper surface: White Group 155B. At the basal zone Green-White Group 157D. Lower surface: White Group 155B. At the basal zone Green-White Group 157A.

*After opening, inner petals.*—Upper surface: White Group 155B. At the basal zone Green-White Group 157D. Lower surface: White Group 155B. At the basal zone Green-White Group 157A.

*Basal petal spots, after opening.*—No distinctive coloration at the petal base observed.

Petals:

*Petal reflex.*—Somewhat reflexed.

*Margin.*—Entire and uniform. No undulations.

*Shape.*—Broad and elliptic. Apex shape: Rounded, with occasional point at the center of the margin. Base shape: Obtuse.

*Size.*—26 mm (l)×25 mm (w).

*Texture.*—Smooth.

*Thickness.*—Average.

Petaloids:

*Size.*—10 mm (l) by 7 mm (w).

*Quantity.*—About 10.

*Shape.*—Elliptical with an acute base and rounded apices.

*Color.*—Yellow-Green Group 154D and Green-White Group 157D.

Reproductive flower parts:

*Pollen.*—None observed.

*Anthers.*—Size: 2 mm in length. Color: Greyed-Yellow Group 162A. Quantity: 45 on average.

*Filaments.*—Color: Green-Yellow Group 145C Length: 3 mm.

*Pistils.*—Length: 6 mm. Quantity: 30 on average.

*Stigmas.*—Color: Green-Yellow Group 145C.

*Styles.*—Color: Green-Yellow Group 145C.

*Location of stigmas.*—Even in location relative to the length of the filaments and the height of the anthers.

*Hips.*—None Observed.

PLANT

Plant growth: Upright, compact and well branched. Plants are about 21 cm in height, and 30 cm wide.

Stems:

*Color of juvenile growth.*—Yellow-Green Group 144B.

*Color of mature growth.*—Yellow-Green Group 144A.

*Length.*—Canes are about 8 cm from the base of the plant to the flowering portion.

*Diameter.*—About 5 mm.

*Internodes.*—On mature canes about 25 mm between nodes.

*Surface texture.*—Young wood: Smooth. Older wood: Smooth.

Long prickles:

*Incidence.*—5 prickles per 10 cm of stem.

*Size.*—Average length of prickles on mature stems is 4 mm.

*Shape.*—Upper portion is linear. Lower portion is concave.

*Color*.—Juvenile prickles: Greyed-Orange Group 164C. Mature prickles: Greyed-Orange Group 164C.

Plant foliage:

*Compound leaf*.—75 mm (l)×45 (w).

*Quantity*.—3 leaves per 10 cm of stem on average.

*Leaf bearing angle to the stem*.—45 degrees.

*Color of juvenile foliage*.—Upper side: Yellow-Green Group 144A with marginal intonations of Greyed-Red Group 178B. Lower side: Yellow-Green Group 145B shaded with Greyed-Red Group 178B.

*Color of mature foliage*.—Upper side: Yellow-Green Group 147A. Lower side: Yellow-Green Group 147B.

Plant leaves and leaflets:

*Stipules*.—Size: 10 mm long, mm wide. Quantity: 2 per compound leaf. Shape: Linear, slightly broad based with outward extending apices. Margins: Finely serrated. Color:

*Petiole*.—Length: About 16 mm. Diameter: 2 mm. Upper surface color: Yellow-Green Group 144A. Lower surface color: Yellow-Green Group 144A.

*Rachis*.—Length: About 25 mm. Upper surface color: Yellow-Green Group 144A. Lower surface color: Yellow-Green Group 144A.

*Leaflet*.—Quantity: Normally 5 leaflets. Margins: Serrated. Size: Terminal leaflets are about 31 mm long, 20 mm wide. Shape: Generally elliptical. Base: Rounded. Apex: Acute. Texture: Smooth. Thickness: Average. Arrangement: Odd pinnate. Venation: Reticulate. Glossiness: Not glossy.

*Disease resistance*.—Above average resistance to powdery mildew *Sphaerotheca pannosa* var. *rosae*, downy mildew *Peronospora sparsa*, rust *Phragmidium* spp., black spot *Diplocarpon rosae*, and *Botrytis cinerea* under normal growing conditions.

*Cold hardiness*.—The variety is tolerant to USDA Cold Hardiness Zone 6.

*Heat tolerance*.—The variety has been found to be suitable for climate conditions found in the American Horticulture Society heat zone 7.

I claim:

1. A new and distinct variety of rose plant of the Miniature rose class named 'Poulpar125', substantially as illustrated and described herein, due to its abundant white flowers, disease resistance, and extended period of bloom.

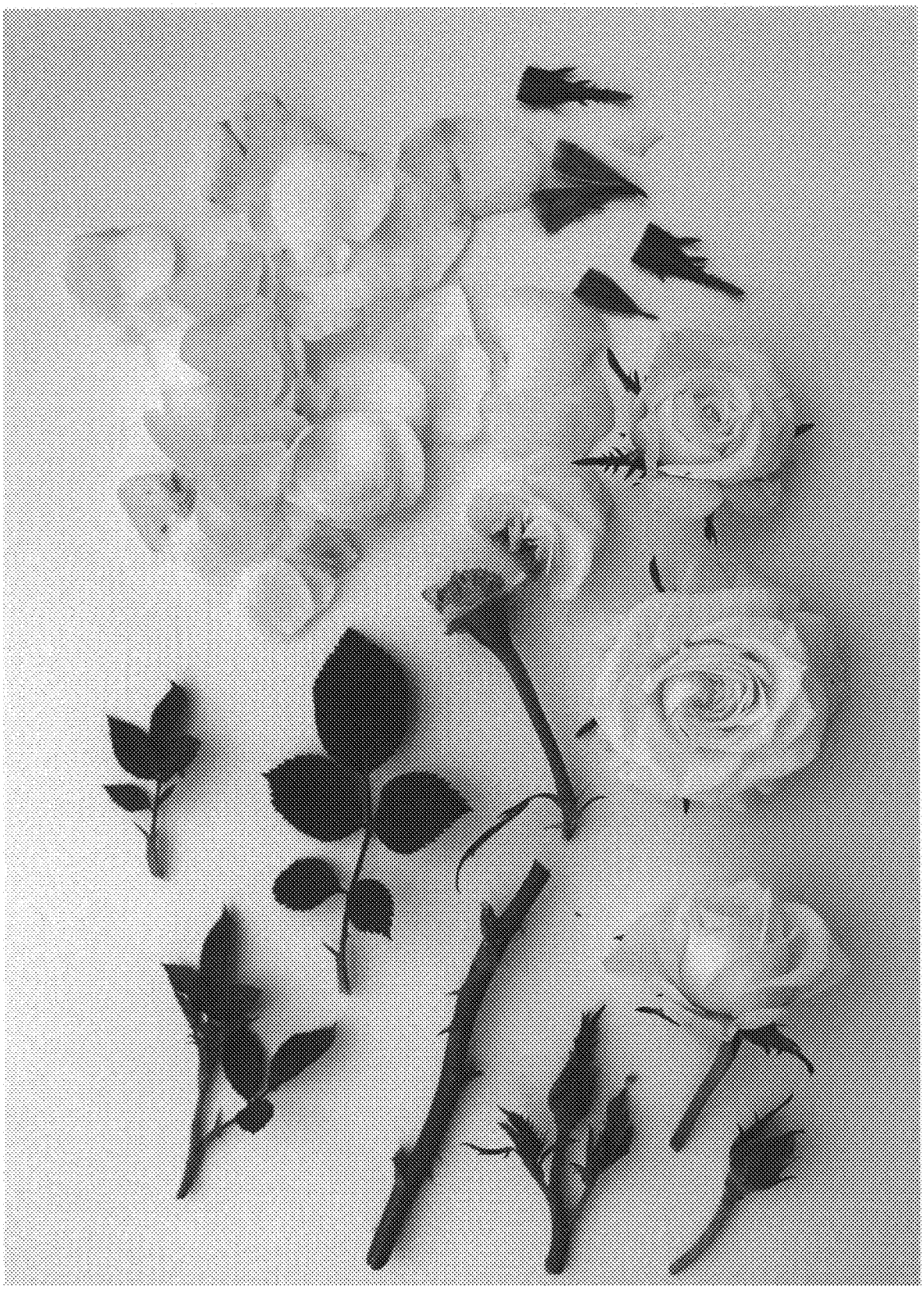

* * * * *